(12) United States Patent
Doorschodt

(10) Patent No.: US 10,874,098 B2
(45) Date of Patent: Dec. 29, 2020

(54) ORGAN PRESERVATION COMPOSITION

(71) Applicant: TX Innovations B.V., Maastricht (NL)

(72) Inventor: Benedict Marie Doorschodt, Amsterdam (NL)

(73) Assignee: TX Innovations B.V., Maastricht (NL)

( * ) Notice: Subject to any disclaimer, the term of this patent is extended or adjusted under 35 U.S.C. 154(b) by 0 days.

(21) Appl. No.: 15/563,634

(22) PCT Filed: Apr. 1, 2016

(86) PCT No.: PCT/NL2016/050228
§ 371 (c)(1),
(2) Date: Oct. 2, 2017

(87) PCT Pub. No.: WO2016/159773
PCT Pub. Date: Oct. 6, 2016

(65) Prior Publication Data
US 2018/0070582 A1 Mar. 15, 2018

(30) Foreign Application Priority Data

Apr. 3, 2015 (NL) .................................... 2014584

(51) Int. Cl.
| | |
|---|---|
| *A01N 1/02* | (2006.01) |
| *C01B 25/30* | (2006.01) |
| *C01D 7/00* | (2006.01) |
| *C07C 229/08* | (2006.01) |
| *C07C 229/24* | (2006.01) |
| *C07C 237/10* | (2006.01) |
| *C07C 309/14* | (2006.01) |
| *C07K 5/083* | (2006.01) |
| *C07K 5/093* | (2006.01) |
| *C08L 71/08* | (2006.01) |

(52) U.S. Cl.
CPC ............ *A01N 1/0226* (2013.01); *C01B 25/30* (2013.01); *C01D 7/00* (2013.01); *C07C 229/08* (2013.01); *C07C 229/24* (2013.01); *C07C 237/10* (2013.01); *C07C 309/14* (2013.01); *C07K 5/0806* (2013.01); *C07K 5/0819* (2013.01); *C08L 71/08* (2013.01)

(58) Field of Classification Search
CPC ........... C07C 15/26; C07C 1/24; C07C 7/005; C07C 7/05; C07C 7/10; C07C 229/08; C07C 229/24; C07C 237/10; C07C 309/14; C07C 2521/04; A01N 1/0226; C01B 25/30; C01D 7/00; C07K 5/0806; C07K 5/0819; C08L 71/08
See application file for complete search history.

(56) References Cited

U.S. PATENT DOCUMENTS

| | | | |
|---|---|---|---|
| 4,784,852 A | 11/1988 | Johansson | |
| 4,873,230 A | 10/1989 | Belzer et al. | |
| 4,879,283 A | 11/1989 | Belzer et al. | |
| 4,920,044 A | 4/1990 | Bretan, Jr. | |
| 4,923,442 A | 5/1990 | Segall et al. | |
| 5,182,299 A | 1/1993 | Gullans et al. | |
| 5,405,742 A | 4/1995 | Taylor | |
| 6,524,785 B1 | 2/2003 | Cozzone et al. | |
| 6,641,992 B2 | 11/2003 | Lopez et al. | |
| 8,637,230 B2 * | 1/2014 | Doorschodt | ......... A01N 1/0226 435/1.1 |
| 2003/0118980 A1 * | 6/2003 | Taylor | ...................... A01N 1/02 435/1.1 |
| 2004/0029096 A1 | 2/2004 | Steen | |
| 2008/0017194 A1 * | 1/2008 | Hassanein | ................. A01N 1/02 128/200.24 |
| 2009/0226876 A1 | 9/2009 | Thatte et al. | |
| 2009/0306029 A1 * | 12/2009 | De Tommaso | .......... A61K 9/14 514/174 |
| 2011/0065083 A1 * | 3/2011 | Shimko | .................... A01N 1/02 435/1.1 |

FOREIGN PATENT DOCUMENTS

| | | |
|---|---|---|
| EP | 1000541 A1 | 5/2000 |
| WO | 00/32140 A1 | 6/2000 |
| WO | 2006/052133 A2 | 5/2006 |

OTHER PUBLICATIONS

Minor et al. Transpl. Int. (1995) 8: 174-179 (Year: 1995).*
Oriyanhan et al. Heart Vessels (2005) 20: 278-285 (Year: 2005).*
McIntosh et al. J. Molecular Cell. Cardiology (2010) 49: 41-47 (Year: 2010).*
Furst J. Nutrition (2001) 131(9): 2562S-2568S (Year: 2001).*
Baicu, Simona C. et al. "Acid-base buffering in organ preservation solutions as a function of temperature: new parameters for comparing buffer capacity and efficiency", Cryobiology 45:33-48, 2002.
Belzer et al. "Combination perfusion-cold storage for optimum cadaver kidney function and utilization", Transplantation, Feb. 1985; 39(2) Abstract only.
Belzer, F.O. "Evaluation of Preservation of the Intra-Abdominal Organs", Transplantation Proceedings, 25(4):2527-2530, Aug. 1993.
Bessems, Maud et al. "Improved Machine Perfusion Preservation of the Non-Heart-Beating Donor Rat Liver Using Polysol: A New Machine Perfusion Preservation Solution", Liver Transplantation, 11(11):1379-1388, Nov. 2005.
Changani, K.K. et al. "Improved preservation solutions for organ storage: a dynamic study of hepatic metabolism", Transplantation, 68(3):345-55, Aug. 1999.

(Continued)

*Primary Examiner* — Susan M Hanley
(74) *Attorney, Agent, or Firm* — Hoffmann & Baron, LLP

(57) ABSTRACT

An aqueous organ preservation solution includes taurine and L-alanine-L-glutamine and glutamic acid. The organ preservation composition can be stored in a solid state, for example in the form of small particles (e.g. a powder or micronized powder), and be dissolved in water, thereby instantly providing a ready-to-use organ preservation solution.

23 Claims, No Drawings

(56) References Cited

OTHER PUBLICATIONS

Churchill, Thomas A. et al. "Investigation of a Primary Requirement of Organ Preservation Solutions: Supplemental Buffering Agents Improve Hepatic Energy Production During Cold Storage", Transplantation, 65(4):551-559, Feb. 27, 1998.

Gnaiger, E. et al. "Autooxidation of Glutathione in Organ Preservation Solutions", Transplantation Proceedings, 32:14, 2000.

Guler, Leyla et al. "Taurine attenuates lung ischemia-reperfusion injury after lung transplantation in rats", J Anesth, 28:347-353, 2014.

Hoffmann, Tanja et al. "New Strategies and Concepts in Organ Preservation", Eur Surg Res, 54:114-126, 2015.

Kalenski, Julia et al. "Improved Preservation of Warm Ischemia-Damaged Porcine Kidneys after Cold Storage in Ecosol, a Novel Preservation Solution", Ann Transplant, 20:233-242, 2015.

Kingston, R. et al. "The Therapueutic Role of Taurine in Ischaemia-Reperfusion Injury", Current Pharmaceutical Design, 10:2401-2410, 2004.

Oguz, M. et al. "L-Alanin-L-glutamine supplementation improves the outcome after colorectal surgery for cancer", Colorectal Disease, 9:515-520, 2007.

Schreinemachers, M.-C.J.M et al. "First Clinical Experience with Polysol Solution: Pilot Study in Living Kidney Transplantation", Transplantation Proceedings, 45:38-45, 2013.

Schuster, Heidi et al. "Protective effects of glutamine dipeptide and α-tocopherol against ischemia-reperfusion njury in the isolated rat liver", Clinical Nutrition 28:331-337, 2009.

Suszynski, Thomas M. et al. "Persufflation (or Gaseous Oxygen Perfusion) as a Method of Organ Preservation", Cryobiology, 64(3):125-143, Jun. 2012.

Van Slyke, Donald D. "On the Measurement of Buffer Values and on the Relationship of Buffer Value to the Dissociation Constant of the Buffer and the Concentration and Reaction of the Buffer Solution", J. Biol. Chem., 52:525-570, 1922.

\* cited by examiner

ORGAN PRESERVATION COMPOSITION

CROSS-REFERENCE TO RELATED APPLICATIONS:

This application is the National Stage of International Application No. PCT/NL2016/050228 filed Apr. 1, 2016, which claims the benefit of Netherlands Application No. NL 2014584, filed Apr. 3, 2015, the contents of which is incorporated by reference herein.

FIELD OF THE INVENTION

The field of the invention is aqueous organ preservation solutions and methods for preparing aqueous organ preservation solutions for use in maintaining the viability of organs and parts of organs. The field of the invention also encompasses the use of such solutions for preservation purposes of organs, but also for preservation of parts of organs. The field of the invention also encompasses aqueous organ preservation solutions and/or compositions for use in oxygenated preservation of human organs and/or parts thereof. According to the invention, an aqueous organ preservation solution is provided comprising taurine and L-alanine-L-glutamine and glutamic acid. Human organ preservation is useful for transplantation purposes in patients in need of a donor organ and/or parts thereof.

BACKGROUND OF THE INVENTION

Aqueous organ preservation solutions are well known in the art. Aqueous organ preservation compositions according to the invention are compositions that may be used for preservation purposes of organs, but also for preservation of parts of organs. Aqueous organ preservation solutions are used to maintain viability of organs or parts of organs without blood supply outside the body (Churchill et al, "Investigation of a Primary Requirement of Organ Preservation Solutions", Transplantation, vol. 65, 551-559, No. 4, 1998). A preservation solution for solid organs is fundamentally different from a solution for preservation of tissue and/or cells since the solution needs to be applicable for preservation of different cell and tissue types in an organ such as parenchymal, mesenchymal and endothelial cells and tissues that are comprised in intricate three dimensional architectures.

By maintaining viability, the organs or parts of organs, can be used for transplantation. For example, for transplantation of a kidney. The aqueous organ preservation solution can be used to wash out organs and parts of organs by gravitational perfusion, e.g. to wash out remaining remnants of blood, during or after retrieval of an organ from a donor. For example, in order to continuously perfuse the organ with a preservation solution and to provide oxygen to the organ, mechanical perfusion with a preservation solution is applied for kidneys, livers and hearts. Mechanical perfusion can be applied at temperatures between 0 and 40 degrees Centigrade. A preservation solution for perfusion of organs is understood to be fundamentally different from a preservation solution for static storage of organs wherein organs can be simply submerged in a preservation solution. An example well known to those skilled in the art is the University of Wisconsin preservation solution which is commercially available in a composition for mechanical perfusion (Kidney Perfusion Solution-1, KPS-1, Organ Recovery Systems, Itasca, Ill., USA) and in a composition for static storage (Static Preservation Solution-1, SPS-1, Organ Recovery Systems, Itasca, Ill., USA). Both solutions are intended for their designated application purpose.

The organ preservation solution can be used for storage of an organ. For example, by cold static storage preservation or oxygenated preservation. Oxygenated preservation may be a pulsatile or continuous perfusion of said solution through the organ or part thereof. Oxygenated preservation may also be by direct persufflation with oxygen gas or a gas mixture through the vasculature of the organ. The basis behind the intervention of oxygen persufflation, is to provide an adequate oxygen supply to an organ during preservation. Data collected over decades has confirmed that improved oxygenation is better for maintaining the quality of an organ and, in some cases, enables the recovery and resuscitation of reversibly-damaged tissue. Oxygen persufflation in particular exhibits the capacity to improve the metabolic quality of tissue, as measured using a number of methods and in a variety of organs (T. M. Suszynski et al., Persufflation (or gaseous oxygen perfusion) as a method of organ preservation. Cryobiology 2012, June; 64(3):125-43). Organs that may be mechanically perfused, persufflated or statically stored during preservation may comprise the kidney, liver, heart, lung, intestine and pancreas.

It is generally accepted in transplantation medicine that maintaining a high quality of the donor organ will result in a better function and/or a longer lifetime of the organ after transplantation in the recipient. Aqueous organ preservation solutions are also intended to decrease the amount of circulating oxygen free radicals, prevent cell swelling, maintain a physiologic acidity and to prevent ischemia/reperfusion injury and ischemic damage. Aqueous organ preservation solutions are usually maintained at hypothermic temperatures when used for washing, perfusion, persufflation and/or storing an organ or parts of an organ. The solution is intended to reduce the temperature of the organ during washout in order to decrease the metabolism and slow the decay of the ischemic organ, tissue or cells (Belzer et al. "Combination Perfusion-Cold Storage for Optimum Cadaver Kidney Function and Utilization" Transplantation 39(2) 1985 pp. 118-12).

At hypothermic, sub-normothermic or normothermic temperatures, a continuous supply of oxygen is known to those skilled in the art to improve the organ preservation quality and may be required to maintain viability of the organ, tissue or cells (Belzer F O, "Evaluation of preservation of the intra abdominal organs", Transplantation Proceedings, vol 25, No 4 (August) 1993, P 2527-2530)(Hoffmann T, Minor T. New strategies and concepts in organ preservation. Eur Surg Res. 2015; 54(3-4):114-26. Above 0 degrees Centigrade, the supply of oxygen to the perfused organ may become essential.

An aqueous organ preservation solution may have an oncotic pressure similar to the oncotic pressure of human plasma to prevent extravasation of said solution from the blood vessels into the interstitium which may cause tissue edema and obstruction of the vascular bed. In clinical practice, the currently employed preservation solutions were introduced by Collins in 1969, Marshall in 1976 and Brettschneider in 1988 (Changani et al, "Improved Preservation Solutions for Organ Storage", Transplantation, vol. 68, 345-355, No. 3, 1999).

The golden standard of preservation of organs and tissues for transplantation is the University of Wisconsin solution (UW) which was introduced in 1988 by Belzer.

The University of Wisconsin solution is a standard original commercial hypothermic static storage preservation solution with an osmolarity of 320 mosmol/L and a pH of 7.4 which comprises 100 mmol/L lactobionic acid, 0.01 mmol/L allopurinol, 3 mmol/L reduced glutathione, 5 mmol/L adenosine, 30 mmol/L raffinose, 5 mmol/L pentastarch, 5 mmol/L KCl, 25 mmol/L KHPO$_4$ and 5 mmol/L MgSO$_4$.

U.S. Pat. No. 4,784,852 (filing year 1981) describes the supply of selenium to a solution for storage of organs, in media for cell cultivation and in nutritive solutions for storage of blood components. Also the addition of vitamins E, B2, B6 and B12 is described to allow the body to assimilate selenium.

U.S. Pat. No. 4,920,044 (filing year 1988) describes preservation solutions for organs which contain buffers such as potassium phosphate and sodium bicarbonate, magnesium and calcium ions and adenosine. The solutions have a pH of 7.20-7.50 and osmolarity of 255-425 mosm/L.

U.S. Pat. No. 4,923,442 (filing year 1989) describes a substitute for blood in mammalian bodies or parts thereof comprising dextran with a molecular weight of 40.000 dalton to achieve a fluid osmotic pressure essentially equivalent to human plasma. The solution also comprises the buffer N-2-hydroxyethylpiperazine-N'-2-ethanesulfonic acid (HEPES) to maintain a pH of around 7.4, essentially equivalent to human plasma.

U.S. Pat. No. 5,405,742 (filing year 1995) describes blood substitute solutions for purging or maintenance of organs during surgery, or for preserving organs for transplantation. The solutions contain solutes, mannitol, buffers, glutathione, an impermeant anion which is lactobionate, iron-chelating agents, calcium channel blockers such as nicardipine and allopurinol.

U.S. Pat. No. 6,641,992 (filing year 1999) describes an aqueous solution for preserving tissues and organs comprising the colloid polyethylene glycol as an oncotic agent. The solution is further basically equivalent to the UW solution by Belzer and Southard (U.S. Pat. No. 4,879,283 and U.S. Pat. No. 4,873,230, 1988) by means of comprising reduced glutathione, adenosine, raffinose, magnesium, potassium phosphate, sodium, chloride and calcium.

US 2004/0029096 (filing year 2000) describes an evaluation and preservation solution for human and animal organs which comprises, amongst other components, serum albumin, dextran, sodium, potassium and magnesium.

In order to improve the clinically employed aqueous organ preservation solutions, the current inventor devised the polysol solution in 2004 (WO2006052133). This organ preservation and perfusion solution for maintaining donor organ viability comprising a tissue culture medium comprised the features of a) the buffer capacity of the tissue culture medium comprising solution was increased to at least a Beta of 20, and, b) at least one high molecular weight compound was added to increase the oncotic pressure, selected from the group of compounds consisting of: dextran, PEG, hydroxyethylstarch (HES) and albumin, c) the solution has a [Na$^+$] concentration of <140 mM, a [K$^+$] concentration of <25 mM, while the ratio of [Na$^+$] to [K$^+$] was at least 2:1. Physiological oncotic pressure was preferably maintained between 20 to 35 mmHg and physiological osmolarity was preferably maintained between 300 to 400 mOsm. The tissue culture medium was preferably selected from Minimal Essential Medium Eagle (MEM), Dulbecco's Modified Eagle Media (DMEM), RPMI 1640 Media, DMEM/F-12 Media, Hams F-10, Hams F 12, Iscove's Modified Dulbecco's Medium, Leibovitz's L-15 Media, Minimum Essential media with Earle's Salts and Williams E medium, with a preference for Williams Medium E. The polysol solution was found to induce rejection of the donor organ in a study involving transplantation of human kidneys (Schreinemachers M C et al. "First clinical experience with polysol solution: pilot study in living kidney transplantation". Transplant Proc. 2013 January-February; 45(1):38-45) and the use of this solution was therefore discontinued. This polysol solution was based on the culture medium, Williams E, well known to the art.

BRIEF DESCRIPTION OF THE INVENTION

The current inventors have found that in order to prepare a tissue culture medium for use as an organ preservation solution, suitable for preservation of organs at low temperatures, several adjustments, omissions and/or additions should be made as compared to known solutions from the prior art. These adjustments have proven to be particularly useful for oxygenated and static preservation of organs obtained from normally less preferred, sub-optimal donors. The aqueous organ preservation solution in accordance with the invention is understood to be suitable for use in perfusion of an organ or a part thereof. The aqueous organ preservation solution in accordance with the invention may also be termed an aqueous organ perfusion preservation solution instead. The terms aqueous organ preservation solution or aqueous organ perfusion preservation solution can be used interchangeably herein throughout. Said aqueous organ preservation solutions in accordance with the invention as described herein are thus for use in the preservation of organs selected from the group consisting of: kidney, liver, lungs, heart, pancreas, intestine, preferably said organs being human organs. It is understood that organs as well as parts of organs are useful. For example, instead of an entire liver, a part of liver may be used for transplantation or in case of a lung transplant, a part of a lung may be transplanted. It is thus understood that "organs as well as parts of organs are suitable for use of the aqueous organ preservation solutions according to the invention. As long as the said part of an organ has a structure as it is present in an entire organ and comprises blood vessels that allows perfusion to be performed, such organ parts are understood to be suitable. It is also understood that the term "a part" within the context of organs, e.g. a part of an organ, is understood not to relate to isolated cells or layers of tissues or the like that are derived from organs. Such isolated cells or in layers of tissues or the like can be cultured in vitro without mechanical perfusion. Hence, also the use is provided of an organ preservation solution in accordance with the invention for the preservation of organs or a part thereof for use in organ transplantation. Preferably, such use comprises perfusion of said organ or part thereof. Preferably said perfusion comprises gravitational or mechanical perfusion. Preferably, said organ (or part thereof) is selected from the group consisting of kidney, liver, lungs, heart, intestine and pancreas, wherein preferably said organs are human organs.

The current invention provides for an improved aqueous organ preservation solution for application in particular in oxygenated organ preservation which comprises taurine and L-alanine-L-glutamine and glutamic acid. The aqueous organ preservation may have a composition such as used in known aqueous organ preservation solutions and comprises said compounds in addition. Preferably, the aqueous organ preservation comprises a colloid, an anti-oxidant, at least 2 electrolytes, an impermeant, at least 2 amino acids, a vitamin and at least 2 buffer compounds, more preferably the aqueous organ preservation solution comprises at least 2 impermeants and at least two anti-oxidants.

It was found by the inventors in experiments using organs from animal donors that said compounds are advantageous in such compositions for the preservation of organs (Kalenski J et al., Improved Preservation of Warm Ischemia-Damaged Porcine Kidneys after Cold Storage in Ecosol, a Novel Preservation Solution. Ann Transplant 2015; 20:233-242). Also, it was found that addition of taurine and L-alanine-L-glutamine and glutamic acid to said solution was essential for application of said solution in oxygenated persufflation and oxygenated mechanical perfusion preservation of said organs.

Also, it was found that providing an organ preservation composition in a solid state, for example in the form of small particles (e.g. a powder or micronized powder) may be advantageous. Such an organ preservation composition can be dissolved in water, thereby instantly providing a ready-to-use organ preservation solution. This way, possible deterioration of ingredients as present in organ preservation compositions can be avoided, thereby ensuring optimal quality of the aqueous organ preservation solution increasing the viability of organs.

With said aqueous organ preservation solution, oxygenated preservation of organs, parts of organs may be improved and may prevent damage to organs commonly occurring by ischemia, hypoxia, hyperoxia, energy depletion, hypothermia and reperfusion injury.

Definitions

"Micronization" is the process of reducing the average diameter of a solid material's particles. The term micronization is used when the particles that are produced have a size in the range of micrometers, e.g. 100 micrometer or less. Micronization also includes the nanometer scale, e.g. 100 nm or less. Micronization techniques can be based on friction to reduce particle size. Such methods may include milling, bashing and grinding. A typical industrial mill is composed of a cylindrical metallic drum that usually contains steel spheres. As the drum rotates the spheres inside collide with the particles of the solid, thus crushing them towards smaller diameters. In the case of grinding, the solid particles are formed when the grinding units of the device rub against each other while particles of the solid are trapped in between. "Micronized particles", i.e. the particles obtained after micronization, may rapidly dissolve in water.

"Osmolarity" is a measure of the osmotic pressure exerted by a solution across a semi-permeable membrane compared to pure water. Osmolarity is dependent on the number of particles in solution but independent of the nature of the particles. Osmolarity is defined as the number of osmoles (Osm) of solute per (L) of solution (osmol/L or Osm/L). The osmolarity of a solution is usually expressed as Osm/L, in the same way that the molarity of a solution is expressed as "M" (molar). Whereas molarity measures the number of moles of solute per unit volume of solution, osmolarity measures the number of osmoles of solute particles per unit volume of solution.

"Oncotic pressure", in blood plasma the dissolved compounds yield an osmotic pressure. A small portion of the total osmotic pressure is due to the presence of large protein molecules and impermeants; this is known as the "colloidal osmotic pressure", or "oncotic pressure". Because large plasma proteins and impermeants cannot easily cross through the capillary walls, their effect on the osmotic pressure of the capillary interiors will, to some extent, balance out the tendency for fluid to leak out of the capillaries. In conditions where plasma proteins are reduced, e.g. from being lost in the urine (proteinuria) or from malnutrition, or in the case of organs taken out of a body for transplantation and stored in a fluid, the result of the low oncotic pressure can be edema-excess fluid build-up in the tissues. Oncotic pressure is expressed in mmHg (millimeters of mercury pressure). Oncotic pressure can be easily measured in the laboratory with an oncometer (for instance, WEIL 186 Oncometer, Instrumentation Laboratory GmbH, München, Germany). The principle is to have 2 chambers which are enclosed and separated from each other by a semi-permeable membrane which is permeable to water and small MW substances, but not permeable to molecules with a MW greater then 30,000 (ie colloids). Because the capillary wall is permeable to water, but essentially impermeant to the larger plasma proteins and impermeants, these molecules generate an osmotic pressure. Furthermore, since these proteins are negatively charged, they tend to hold additional cations in the plasma (the Gibbs-Donnan effect), further enhancing an osmotic gradient between the plasma and the interstitial fluid (ISF). The combined effect (osmotic pressure and Gibbs-Donnan effect) results in a pressure that draws water out of the interstitium and into the plasma. This pressure is proportional to the difference in protein concentration between the plasma and the ISF. Compared to pure saline, the human plasma exerts about 28 mm Hg oncotic pressure, whereas the ISF has only about 3 mm Hg. The net oncotic pressure is thus about 25 mm Hg. This value remains roughly constant over the length of most capillary beds.

"Impermeants" are negatively charged large molecules such as carbohydrates (for instance raffinose, trehalose, mannitol) which increase the oncotic pressure of a preservation solution. The phenomenon of cell swelling can be counteracted by adding impermeants to the preservation solution. Extravasation of the solution during washout, creating an expansion of the interstitial space, can compress the capillary system and may lead to an uneven distribution of the washout solution throughout the organ. can be prevented by encorporation of a colloid into the solution which allows free exchange of constituents of the washout solution without expansion of the interstitial space.

A "colloid" is a substance microscopically dispersed throughout another substance. For the aqueous solution of the invention, microscopic particles dispersed throughout the aqueous solution. Colloid containing solutions belong to the group of volume expanders, and can be used for intravascular fluid replacement. Colloids preserve a high colloid osmotic pressure in the blood and therefore, they may increase the intravascular volume when used in organ preservation solutions.

A "buffer", i.e. a pH buffer or hydrogen ion buffer, is an aqueous solution consisting of a mixture of a weak acid and its conjugate base, or a weak base and its conjugate acid. The pH of a buffer changes little when strong acid or base is added to it. Buffers are used prevent changes in the pH of a solution. Buffers are thus very important components in organ preservation and perfusion solutions, by maintaining a constant pH, i.e. hydrogen ions, within the physiological range. The pH of mammalian blood is maintained close to 7.38, i.e. close to a range of 7. by a buffer system that includes $H_2PO_4^- \Leftrightarrow HPO_4^{2-}$ and $H_2O+CO_2 \Leftrightarrow H_2CO_3 \Leftrightarrow HCO_3^- + H^+$.

Buffers according to the invention that are universally applicable and biologically acceptable for the solution according to the current invention must display water solubility, no interference with biological processes or known complex-forming tendency with metal ions, non-toxicity and no interference with biological membranes (such as penetration, solubilisation, adsorption on surface). The buffer capacity is influenced by temperature and other solutes in the composition. Activity and salt effects have a marked influence on the pH value of a solution according to the equation:

$$pH = pKa' + \log[B]/[BH] \quad (1)$$

where pKa'=pKa+correction factor. Ionic strength of a solution is defined as in $$I = 1/2 \Sigma(c_i z^2)$$

where $c_i$ is the concentration of species i, and z is the corresponding charge. It can be calculated. Buffer Capacity is the ratio of the increment of strong base or strong acid to the change in pH.

$$B = \Delta B/pH$$

where the small increment in gram equivalents/liter of strong base (or acid) added to buffer solution to produce a pH change of $\Delta pH$.

$$B = (2.3 \times C \times K_a[H^+])/(K_a + [H^+])^2$$

$$B = 2.3 Ca(1-a)$$

$$C = [Acid] + [Salt] \text{ or } C = [Base] + [Salt]$$

The maximum buffer capacity Beta-max of a monovalent species is found to be at pH=pKa', the practical pK-value. Beta max in the pH range 3-11 is calculated according to equation: Beta max=0.576 c, where c is the total concentration of the buffer substance.

Thus a useful buffer capacity lies within a pH range of pKa±1 unit. If more than 50% of the maximum buffer capacity must be realized, the corresponding range is only pKa'+0.75 units. The buffer capacity of a solution can also be expressed in Slykes units. Buffering capacity, measured in slykes, is defined as the mmoles of base required to titrate the pH of 1 g wet mass of muscle/tissue by 1 pH unit, over the pH range 6 to 7 (Van Slyke, Biol. Chem. 52, 525-570, 1922). For this application the Beta is defined as the µmoles of sodium hydroxide or hydrogen chloride required to change the pH of one gram of tissue by one unit, i.e., from 6 to 7 or from 6.5 to 7.5.

DETAILED DESCRIPTION OF THE INVENTION

According to the invention, an aqueous organ preservation solution is provided comprising taurine and L-alanine-L-glutamine and glutamic acid. Preferably the organ preservation solution further comprises a colloid, anti-oxidants, electrolytes, impermeants, amino acids, vitamins and a buffer compound. The aqueous organ preservation solution can be used to wash organs, e.g. to wash out remaining remnants of blood, during or after retrieval of an organ, or a part thereof from a donor. Hence, the aqueous organ preservation solution may be used as a perfusion solution. After washing, the organs may be preserved in the aqueous organ preservation solution for periods longer than possible with currently used preservation solutions and techniques. In Example 3, it is shown that organs that have sustained extensive damage can be maintained vital for transplantation for 24 hours by oxygenated persufflation and/or oxygenated mechanical perfusion using said solution, in contrast to the currently used gold standard static, unoxygenated organ preservation method. The aqueous organ preservation solution in accordance with the invention may also be termed an aqueous organ perfusion preservation solution instead. As said, the terms aqueous organ preservation solution or aqueous organ perfusion preservation solution can be used interchangeably herein throughout. Also, said aqueous organ preservation solution in accordance with the invention is for use in perfusion, such as gravitational and/or mechanical perfusion, of organs or parts of organs, such as shown in the examples.

Hence, also provided is the use of an aqueous organ preservation solution according to the invention comprising taurine and L-alanine-L-glutamine and glutamic acid for the preservation of an organ or part thereof for transplantation.

Furthermore, the use is provided of an aqueous organ preservation solution according to the invention comprising taurine and L-alanine-L-glutamine and glutamic acid for the preservation of an organ or a part thereof for transplantation, wherein said preservation of organs comprises perfusion with the aqueous organ preservation solution of said organ or said part thereof. In a further embodiment, said perfusion comprises gravitational and/or mechanical perfusion. In another further embodiment said perfusion comprises oxygenated perfusion. Such perfusion is described in the examples. Gravitational perfusion can be performed on the organ when it has been obtained from the body, e.g. the human body, when the organ has been separated from the body. To the provided organ, tubing is attached e.g. to a main artery, the other end being attached to a container having the aqueous organ preservation solution. By holding the container above the organ, e.g. about a meter higher, the aqueous organ preservation solution perfuses the organ. Once the organ has been perfused, the organ may be stored upon, e.g. in a cooled container. The perfusion may also be mechanical. In mechanical perfusion a pump can be used to perfuse the organ. Such is for instance useful for transport of the organ. The organ (or part thereof) can then be continuously perfused during transport and/or storage up until transplantation. The aqueous organ preservation solution can then be recirculated through the organ. In such a scenario, oxygenation of the aqueous organ preservation solution may be advantageous.

According to the invention, taurine, L-alanine-L-glutamine and glutamic acid are suitable for inclusion in any aqueous preservation solution for use in the preservation of organs or parts of organs by means of static cold storage, oxygenated storage or preservation by gravitational or mechanical perfusion of said organs or parts of organs can be highly advantageous. In particular, according to the invention, taurine, L-alanine-L-glutamine and glutamic acid are suitable for inclusion in aqueous preservation solutions for use in the preservation of organs or parts of organs by means of static cold storage oxygenated storage or preservation by mechanical perfusion of said organs, or parts of organs is highly advantageous.

In one embodiment, the aqueous organ preservation solution comprises taurine, L-alanine-L-glutamine and glutamic acid.

In oxygenated preservation of organs and parts of organs, anti-oxidant therapy is essential for protection against damage caused by formation of free oxygen radicals and lipid peroxidation. Successful application of oxygenated preservation of organs and parts of organs may require an appropriate anti-oxidant and appropriate application of said anti-oxidant.

Taurine, the major intracellular free amino acid found in high concentrations in mammalian cells, is an endogenous antioxidant and a membrane-stabilizing agent. In a previous study, it was demonstrated that taurine may be effective in reducing oxidative damage and ischemia-reperfusion injury after lung transplantation (Guler L et al., Taurine attenuates lung ischemia-reperfusion injury after lung transplantation in rats. Anesth. 2013 November 6). Three days before the harvesting procedure of the lung, taurine was administered intraperitoneally into the donor animal. The organ was then removed from the donor animal, washed out with an aqueous preservation solution and transplanted into a recipient animal. It was demonstrated that intraperitoneal treatment of the donor animal with taurine resulted in preservation of the transplanted lung in respect to histopathological and biochemical findings. In the current invention, taurine is incorporated into the aqueous preservation solution to protect the organ and/or tissue against oxidative damage during preservation and against subsequent hyperoxic reperfusion injury when the organ or tissue is transplanted into the recipient. Also, since pre-treatment of a human organ donor before harvesting is not feasible and prohibited by current laws, anti-oxidative treatment of an organ or tissue for transplantation can only be applied by addition of an anti-oxidative agent into the aqueous washout and preservation solution.

In organ (and parts thereof) preservation and in particular in oxygenated organ preservation, the provision of oxygen to cells, tissue or an organ increases the cell and tissue metabolism as known to those skilled in the art and demonstrated in Example 3. An increased cell and tissue metabolism results in depletion of nutrients for energy production, hence, restoration of energy sources is essential for maintaining organ viability, in particular regarding oxygenated preservation of organs and/or parts of organs for transplantation, L-glutamine is a conditionally essential amino acid and a vital nutrient in cell cultures for energy production as well as protein and nucleic acid synthesis. L-glutamine further plays a role in regulation of acid-base balance, cellular energy as a source next to glucose, nitrogen donation for anabolic processes including the synthesis of purines and carbon donation, as a source for refilling the citric acid cycle.

L-alanine plays an essential role in the glucose-alanine cycle. In tissues that degrade amino acids for fuel, amino groups are collected in the form of glutamic acid by transamination. Glutamic acid can then transfer its amino group through the action of alanine-aminotransferase to pyruvate, forming alanine and α-ketoglutarate.

L-glutamine and L-alanine in aqueous solutions spontaneously degrade, generating ammonia and pyrrolidone carboxylic acid as byproducts. L-alanine-L-glutamine, is more stable in aqueous solutions and does not spontaneously degrade (Oguz et al. "L-alanin-L-glutamine supplementation improves the outcome after colorectal surgery for cancer", Colorectal Dis. 2007 July; 9(6):515-20). The mechanism of dipeptide utilization involves the gradual release of peptidase to allow the gradual hydrolysis of the dipeptide in the medium. This can be compared to the strategy of a fed-batch culture in which L-glutamine is continuously fed into the culture but maintained at low concentration. The result is an efficient energy metabolism.

Glutamic acid is a key compound in cellular metabolism. In humans, dietary proteins are broken down by digestion into amino acids, which serve as metabolic fuel for other functional roles in the body. A key process in amino acid degradation is transamination, in which the amino group of an amino acid is transferred to an α-ketoacid, typically catalysed by a transaminase. The reaction can be generalised as such:

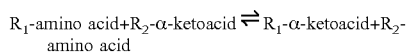

A very common α-ketoacid is α-ketoglutarate, an intermediate in the citric acid cycle. Transamination of α-ketoglutarate provides glutamic acid. The resulting α-ketoacid product can contribute as fuel or as a substrate for further metabolism processes. An example is as follows:

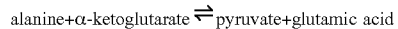

Both pyruvate and α-ketoglutarate are key components of cellular metabolism, contributing as substrates or intermediates in fundamental processes such as glycolysis, gluconeogenesis, and the citric acid cycle.

An aqueous solution comprising at least taurine and L-alanine-L-glutamine and glutamic acid not been previously devised for organ and/or parts of organs and/or tissue preservation for transplantation applications.

In Example 2, a study is provided for the assessment of Example Solution 2 (ES2), an organ preservation solution according to the invention, without comprising taurine, L-alanine-L-glutamine and glutamic acid. The results were compared with CS using Histidine-Tryptophan-Ketoglutarate, the clinical gold standard cold storage preservation solution. To this end, both preservation solutions were assessed using the isolated perfused porcine kidney model (IPPK) employing warm ischemically damaged (WI) kidneys. The ES2 preservation solution was compared to HTK for 24-hour CS preservation of 45 minutes WI damaged kidney grafts, employing non-WI damaged kidneys, cold stored for 24-hour in HTK as controls. Kidney function was significantly lower in ES2-WI and HTK-WI compared to controls as expressed by lower creatinine clearance rates and lower urine production. Also, renal tubular function was significantly lower in ES2-WI and HTK-WI compared to controls as reflected by fractional excretion of sodium. ES2 preserved WI-damaged grafts demonstrated significantly lower IRR, urinary protein concentrations and higher oxygen consumption compared to HTK-WI.

In Example 3, the same organ preservation solution composition was tested as compared to Example 2 but now including taurine, L-alanine-L-glutamine and glutamic acid. An assessment was made of the Example Solution (ES) for venous systemic oxygenated persufflation (VSOP), oxygenated mechanical perfusion (MP), and cold storage (CS) preservation of kidneys for transplantation. The results were compared with CS using Histidine-Tryptophan-Ketoglutarate preservation solution (HTK), the clinical gold standard organ preservation solution worldwide. VSOP, MP and CS using ES preservation solution were compared to HTK for 24-hour preservation of 45 minute warm ischemia (WI) damaged kidney grafts, employing non-WI damaged kidneys, cold stored for 24 hour in HTK as controls. Renal function and renal tubular injury did not differ significantly in the VSOP-ES, MP-ES and CS-ES groups from the non-warm ischemically damaged controls. Urine production was significantly higher in the VSOP-ES, MP-ES and CS-ES groups compared to CS-HTK. Reduced lipid peroxidation was observed in VSOP-ES and CS-ES compared to CS-HTK, with concentrations similar to controls. This study demonstrated the superiority of ES preservation solution for VSOP, MP and CS in comparison to the gold standard HTK solution as well as improvement of oxidative status and metabolic and functional recovery of WI-damaged kidney grafts. ES preservation solution in particular in combination with VSOP resulted in improved preservation quality of WI-damaged kidneys which was comparable to non-WI damaged kidneys using HTK.

From the comparisons made in Examples 2 and 3, it can be concluded that inclusion of taurine, L-alanine-L-glutamine and glutamic acid in an organ preservation solution proved to be highly advantageous as renal function significantly improved and resulted in less oxidative stress resulting in a quality of WI-damaged kidneys comparable to non-WI damaged kidneys.

In one embodiment, the aqueous organ preservation solution also comprises biotin (vitamin H). Biotin is a water-soluble vitamin that is generally classified as a B-complex vitamin. After the initial discovery of biotin, nearly 40 years of research were required to establish it as a vitamin. Biotin is required by all organisms but can be synthesized only by bacteria, yeasts, molds, algae, and some plant species. Biotin is attached at the active site of five mammalian enzymes known as carboxylases. The attachment of biotin to another molecule, such as a protein, is known as "biotinylation." Holocarboxylase synthetase (HCS) catalyzes the biotinylation of apocarboxylases (i.e., the catalytically inactive form of the enzyme) and of histones (See below). Biotinidase catalyzes the release of biotin from histones and from the peptide products of carboxylase breakdown. Each carboxylase catalyzes an essential metabolic reaction:

- Acetyl-CoA carboxylase I and II catalyze the binding of bicarbonate to acetyl-CoA to form malonyl-CoA. Malonyl-CoA is required for the synthesis of fatty acids. The former is crucial in cytosolic fatty acid synthesis, and the latter functions in regulating mitochondrial fatty acid oxidation.
- Pyruvate carboxylase is a critical enzyme in gluconeogenesis—the formation of glucose from sources other than carbohydrates, for example, amino acids.
- Methylcrotonyl-CoA carboxylase catalyzes an essential step in the catabolism of leucine, an essential amino acid.
- Propionyl-CoA carboxylase catalyzes essential steps in the metabolism of certain amino acids, cholesterol, and odd chain fatty acids (fatty acids with an odd number of carbon molecules) (4).

Histones are proteins that bind to DNA and package it into compact structures to form nucleosomes-integral structural components of chromosomes-. The compact packaging of DNA must be relaxed somewhat for DNA replication and transcription to occur. Modification of histones through the attachment of acetyl or methyl groups (acetylation or methylation) has been shown to affect the structure of histones, thereby affecting replication and transcription of DNA. Mounting evidence indicates that biotinylation of histones plays a role in regulating DNA replication and transcription as well as cellular proliferation and other cellular responses. Biotin has not been previously incorporated in organ preservation solutions or for other transplantation applications.

In one embodiment, the aqueous organ preservation solution also comprises glutathione disulfide (GSSG). The aqueous organ preservation solution may comprise glutathione (GSH) and (GSSG). The aqueous organ preservation solution may comprise glutathione (GSH). Hence, the aqueous organ preservation solution according to the invention may comprise glutathione (GSH) and/or glutathione disulfide (GSSG). GSSG is a disulfide derived from two GSH molecules. In living cells, GSSG is reduced into two molecules of GSH with reducing equivalents from the coenzyme NADPH. This reaction is catalyzed by the enzyme glutathione reductase Antioxidant enzymes, such as glutathione peroxidases and peroxiredoxins, generate GSSG during the reduction of peroxides such as hydrogen peroxide ($H_2O_2$) and organic hydro peroxides (ROOH)

$$2GSH+ROOH \rightarrow GSSG+ROH+H_2O$$

Other enzymes, such as glutaredoxins, generate glutathione disulfide through thiol-disulfide exchange with protein disulfide bonds or other low molecular mass compounds, such as coenzyme A disulfide or dehydroascorbic acid

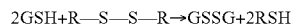

$$2GSH+R\text{—}S\text{—}S\text{—}R \rightarrow GSSG+2RSH$$

Amongst others, U.S. Pat. No. 4,873,230 (filing date 1989) describes the incorporation of GSH as an anti-oxidant in organ preservation solutions. GSSG is not known to have anti-oxidative properties. Not being bound by theory, GSSG is suggested to be a substrate of the forming of anti-oxidants in the liver and may shift the balance of degradation of GSH, resulting in increased availability of GSH in tissue. GSSG has not been previously incorporated in organ preservation solutions or for other medical applications.

In another embodiment, it was found that an aqueous organ preservation solution when comprising several amino acids, peptides and/or colloids may increase the efficacy of the solution for use in organ preservation and may prevent the immunologic response of the recipient of the graft.

In another embodiment, it was found that an aqueous organ preservation solution when comprising several impermeants, may increase the efficacy of the solution and may prevent extravasation of the solution into the interstitium of the donor organ and may prevent cell swelling, which may result in patent blood vessels and highly effective wash out of donor blood remnants from the donor organ. An aqueous organ preservation solution comprising more than one impermeant has not been previously been described in organ preservation solutions or for other medical uses.

An aqueous organ preservation solution, which may also be used as a perfusion solution, according to the current invention may also have a specific and optimized balance of $[Na^+]$ to $[K^+]$ concentrations. Under normal physiological circumstances the intracellular concentration of $[K^+]$ is significantly higher than the intracellular concentration of $[Na^+]$, whereas the situation in the interstitial lumen is the reverse. The organ preservation and perfusion solution according to the current invention is preferably designed to mimic the physiological extracellular concentration, such that the organ, tissues and cells may be facilitated to maintain a physiological $[Na^+]/[K^+]$ balance which is important for driving, among others, the ionic transport conducted by sodium pumps. The imbalance in intracellular and extracellular $[Na^+]$ on $[K^+]$ concentrations creates both an electrical and chemical gradient across the plasma membrane. This may be important not only for the cell but, in many cases, also for directional fluid and electrolyte movement across epithelial sheets.

The $Na^+K^+$ ATPase is a highly-conserved integral membrane protein that is expressed in virtually all cells of higher organisms. It provides the driving force for several facilitated transporters, which import glucose, amino acids and other nutrients into the cell. Without being bound by theory, this transport has proven to be of importance for low temperature preservation and perfusion of organs, in particular for organs from non-heart-beating donors, by the experiments conducted by the current inventors. Translocation of sodium from one side of an epithelium to the other side creates an osmotic gradient that drives absorption of water. Important instances of this phenomenon can be found in the absorption of water, for instance from the lumen of the small intestine and in the kidney. Therefore, preferably the aqueous organ preservation solution according to the current invention mimics the physiological extracellular [Na$^+$]/[K$^+$] balance of at least 2:1, preferably 3:1 and more preferably 5:1.

Another compound that may be comprised in the aqueous organ preservation solution and perfusion solution according to the current invention is a high molecular weight compound to provide for oncotic pressure. Several high molecular weight additives that can be advantageously used in organ preservation and perfusion solutions are known in the art, such as polyethylene glycols (PEG) and modifications thereof (U.S. Pat. No. 4,938,961 and U.S. Pat. No. 5,599,659), dextrans, serum proteins such as albumins, hydroxyethylstarch (HES), and other high molecular weight sugars and biocompatible polymers of net negative charge in pH neutral solutions.

Because large plasma proteins cannot easily cross through the capillary walls, their effect on the osmotic pressure of the capillary interiors may, to some extent, balance out the tendency for fluid to leak out of the capillaries. In conditions where plasma proteins are reduced, e.g. for instance in case of organs taken out of a body for transplantation purposes and stored in a preservation fluid, the result of the too low oncotic pressure is edema excess fluid buildup in the tissues. This problem needs to be addressed, in particular for organs obtained from non-heart-beating donors which often are in a slightly deteriorated condition. Therefore, negatively charged high molecular weight molecules can be added, to maintain a physiological oncotic pressure, which is expressed in mm Hg (millimeters of mercury pressure). Preferably the organ preservation and perfusion solution of the current invention yields an oncotic pressure of 20 to 30 mmHg, preferably around physiological levels, close to 25 mmHg. In one embodiment, PEG is used as a high molecular weight additive in organ preservation solutions of the current invention. In a most preferred embodiment PEG of a molecular weight in the range of 25,000 to 50,000 Dalton is used, preferably at concentrations in the range of 1-50 grams per Liter, 10 to 50 grams per Liter, 10 and 35 grams per Liter, or between 10 and 30 grams per Liter. Other high molecular weight compounds such as HES, albumins and dextrans may also be advantageously used for generating oncotic pressure, optionally in combination with PEGs.

Control of pH to prevent undesired intracellular pH increase or decrease are of importance for aqueous organ preservation solutions and perfusion solutions. Ischemia, hypoxia, energy depletion and hypothermia are factors that can result in a drop of pH levels and may lead to acidification of cells, tissues and organs to be transplanted. Acidification is a widely recognized hazard for organs, tissues and cells and can result in quick deterioration of the condition of the organ to be transplanted (Baicu and Taylor, 2002 Cryobiology 45 p. 33-48). Acidity is in particular a problem that may need to be addressed for organs obtained from non-heart-beating donors, which already have experienced ischemia, hypoxia and depletion of nutrients. The aqueous organ preservation solutions according to the invention are optimized such that they may address and overcome such problems.

Providing additional buffer capacity to the aqueous organ preservation solution of the invention to prevent acidification of the organ stored at low temperature and with no or a decreased artificial perfusion, can be another feature of the aqueous organ preservation solution and perfusion solution of the invention. Although tissue culture media often have a biologically acceptable buffer optimized for a physiological pH between the range of pH 7.0 and pH 7.8, preferably around pH 7.4 at physiological temperatures of around 37° C., additional buffering capacity may be required for the above mentioned reasons (Baicu et al. "Acid-base buffering in organ preservation solutions as a function of temperature: new parameters for comparing buffer capacity and efficiency", Cryobiology 2002, 45 p. 33-48). Hence an aqueous organ preservation solution and perfusion solution for low temperatures, between 0° Centigrade and 21° Centigrade, according to the current invention is provided with a buffering system with a minimum capacity (Beta) of at least 20, more preferably at least 25, 30, 35, 40, or 50 and most preferably at least 30 to 35 as measured in Slykes units (slykes unit=(millimoles acid added per unit change to pH)).

Biologically and physiologically acceptable buffers that have a suitable pKa range and may be advantageously used in solutions according to the current invention can be selected from the group consisting of HEPES, PIPES, MOPS, TES, BES, Bicine, Tricine, Tris, Citrate, Histidine, $KH_2PO_4$, $K_2HPO_4$, $NaHCO_3$ and other phosphate-, citrate- and carbonate-buffers, known and well documented in the art (Current Protocols, Wiley Interscience, 2004). HEPES is the most preferred buffer in solutions according to the current invention to provide the desired (additional) buffer capacity, preferably at concentrations between 1000-10000 mg/L, most preferably between 2500 and 7500 mg/L.

The pH of the organ preservation may be adjusted using $Mg(OH)_2$, NaOH, KOH, $Ca(OH)_2$ or combinations thereof, to obtain a pH between 7 and 8, most preferably between 7.3 and 7.5 at 0-21 degrees Centigrade.

In another embodiment, an aqueous organ preservation solution is provided according to the invention comprising one or more selected from the group consisting of, or all selected from the group consisting of:

I) at least one colloid such as a dextran or polyethylene glycol;
II) at least two buffer compounds with pH buffer properties such as potassium phosphate, sodium phosphate, sodium bicarbonate, sodium citrate, histidine or N-2-hydroxyethylpiperazine-N'-2-ethanesulfonic acid;
III) at least one, preferably two components with impermeant properties, such as sodium gluconate, magnesium gluconate, potassium gluconate, calcium gluconate, mannitol, raffinose, lactobionic acid, ribose or trehalose;
IV) at least one vitamin such as vitamin B1, vitamin B3, vitamin B6, vitamin B12, vitamin C or vitamin E;
V) at least one electrolyte such as sodium, potassium, calcium, chloride or magnesium ions;
VI) at least one component of the energy supply system such as 5'-(N-ethylcarboxamido)adenosine, adenosine, glucose, adenine and pyruvate;
VII) at least one substrate for the formation of antioxidants such as glutathione disulfide; and/or glutathione; and/or taurine
VIII) one or more amino acids, such as histidine, cysteine, carnitine, glycine, glycyl-glutamine, arginine, ornithine and tryptophan The composition may comprise all of the I)-VIII) as listed.

In another embodiment, the aqueous organ preservation solution of the invention may comprise one or more compounds selected from:
I) at least one component with iron chelating properties, such as deferoxamine or EDTA; and
II) at least one or more oxygen free radical inhibitors such as trolox, allopurinol or reduced glutathione The concentration for the electrolytes preferably may be: sodium: 50-150 mmol/L; potassium: 0-25 mmol/L; chloride: 0-50 mmol/L; calcium: 0-5 mmol/L; magnesium: 0-10 mmol/L.

In one embodiment, a buffer compound may be selected from the group consisting of sodium bicarbonate, sodium phosphate, sodium citrate, Histidine, potassium phosphate or N-2-hydroxyethylpiperazine-N'-2-ethanesulfonic acid, preferably N-2-hydroxyethylpiperazine-N'-2-ethanesulfonic acid. The herein described aqueous organ preservation solution has a pH preferably in the range of 7.0-7.8, more preferably in the range of 7.3-7.5 and most preferably 7.4.

Preferably the herein described solution or prepared solution may have an osmolarity in the range of 250-420 mosmol/L, more preferably in the range of 380-410 and most preferably in the range of 390-400 mosmol/L.

An anti-oxidant or combination thereof may be selected from any known anti-oxidant such as taurine, vitamin C, vitamin E, reduced glutathione, oxidized glutathione or vitamin C, preferably taurine.

Additionally, functional equivalents to those listed above may be contemplated.

All compounds as described herein are classified as non-pharmacopoeia substances which may have the advantage that certification for clinical application is facilitated.

The organ preservation composition may be manufactured by methods as known in the art, and as described herein, for example by mixture of the components and thereafter micronization into powder under pharmacopoeia acceptable conditions. The micronization process may have the advantage that said powder can be stored for extended periods without significant loss of quality. Before application, the powder can be rapidly and thoroughly dissolved in water.

The current invention provides a kit, aqueous organ preservation solution and organ preservation composition for use of preservation of the kidney, liver, lung, heart, pancreas, and intestine, as well as for preservation of parts of these organs.

The current invention provides a kit, comprising an aqueous organ preservation solution or organ preservation composition according to the invention for use of preservation of the kidney, liver, lung, heart, pancreas, and intestine or a part of said organs. Said use being preferably for use in mechanical perfusion.

In one embodiment of the invention there is provided a method for preservation of said organs or part of organs at hypothermic temperatures. These methods may be at sub-normothermic or at normothermic temperatures. Organ preservation solutions currently available do not allow the application at a broad temperature range, being hypothermic, sub-normothermic and normothermic temperatures.

In one embodiment of the invention there is provided a method for preservation of said organs or part of organs by means of hypothermic static storage preservation as well as in combination with mechanical perfusion of an organ or parts of an organ. It is known to those skilled in the art that preservation solutions currently commercially available do not hold the capability of preservation of organs, parts of organs, tissues and cells by means of both static cold storage and preservation by mechanical perfusion of said organs or parts of organs.

In one embodiment of the invention there is provided a method for preservation of said organs, by means of hypothermic static storage preservation, preferably in combination with mechanical perfusion of an organ, or part of an organ. Aqueous preservation solutions are provided in the art have described the basis for preservation solutions with also the addition of components for the specific use at hypothermic or normothermic conditions and application in static preservation or mechanical perfusion. According to the invention, an aqueous organ preservation solution can be provided, not by providing a ready-to-use solution, but rather by providing an organ preservation composition. Such a composition can be readily dissolved, for example in sterile water, thereby obtaining an aqueous organ preservation solution. Hence, the organ preservation composition may comprise all the solutes and/or components as present in the aqueous organ preservation solution, i.e. without having a significant amount of water (no liquid water is present). It is also understood that the aqueous organ preservation solution may be prepared by using any suitable components, and that such can be comprised in the organ preservation composition. Components may be provided in free form or in any appropriate salt or acid thereof. For example, glutamic acid may be provided in free form or as sodium glutamate. Any appropriate and suitable form of components may be used, taking into account the metes and bounds of organ preservation solutions with regard to physiological compatibility (e.g. electrolyte composition, pH, osmolarity, oncotic pressure) well known to the skilled person and such as described and defined herein.

Furthermore, in particular the composition may be in the form of a micronized powder. The herein described invention therefore comprises substances which are known to biocompatible, stable at temperatures between 0 and 40 degrees Centigrade and not toxic to the liver, kidney, heart, lung, pancreas and intestine. The supply in solid form, e.g. micronized powder, has the advantage of a shelf life of two years minimally. From prior art and preservation solutions applied commercially, it is known that shelf life is limited to one year at most. Several vital components used in current preservation solutions, for instance reduced glutathione and glutamine, are known to degrade or oxidize shortly after manufacturing of the preservation solution in liquid form (Gnaiger et al., "Autooxidation of Glutathione in organ preservation solutions", Transplantation Proceedings, 32 (2000) 14). The current invention holds the advantage that the preservation solution stored in micronized powder form can be rapidly dissolved and stored for extended periods of time without degradation or oxidation of its components. Another advantage may be that the volume required for storage may be reduced significantly.

Furthermore, the current invention also contemplates any aqueous organ preservation solution currently used in clinical practice, for preparing a solid form (such as a powder or a micronized powder) thereof, i.e. providing an organ preservation composition thereof. Such compositions may have the advantage over the existing solutions currently provided as having a longer shelf life, but also having an improved effect on viability of organs (or tissue or cells) as the solution is freshly made and thus does not suffer from deterioration.

The organ preservation composition may be dissolved in sterile water at hypothermic temperatures (between 0 and 10 degrees Centigrade), at sub-normothermic temperatures (between 10 and 34 degrees Centigrade) or at normothermic, physiologic temperatures (between 34 and 40 degrees Centigrade), but higher temperatures, up to the boiling point of water, may be contemplated, as long as it is not detrimental to the constituents.

In further embodiments, a use is provided of an aqueous organ preservation solution or organ preservation composition according to the invention for the preservation of an organ or parts of an organ. Preferably said aqueous organ preservation solution or organ preservation composition according to the invention is for the preservation of an organ or a part of an organ. In still further embodiments, said provided use is for the preservation of an organ or parts of an organ, wherein these are of human origin. Preferably said provided use is for the preservation of an organ, or a part of an organ wherein these are of human origin. Preferred organs or parts thereof are selected from the group consisting of kidney, liver, lung, heart, pancreas and/or intestine. Preferably said use of an aqueous organ preservation solution or organ preservation composition according to the invention is for the preservation of an organ or a part thereof wherein said preservation comprises mechanical or gravitational perfusion.

EXAMPLES

Example 1

Example of the aqueous organ preservation solution according to the current invention (Example Solution, ES). In the table below, the concentration, as well as the concentration range of the compounds is listed. The amounts used (mg/L) in examples 2 and 3 are listed for Example Solution 2 (ES2) and Example Solution (ES).

The compounds were dissolved in sterile water for injection.

| Compound | mg/L (ES & ES2) | Range (mg/L) |
|---|---|---|
| Polyethyleneglycol-PEG 10-35.000 Dalton | 19000 | 1000-50000 |
| Sodium Gluconate | 6100 | 1000-15000 |
| Magnesium D-Gluconate | 5000 | 1000-10000 |
| Taurine (not in ES2) | 4600 | 1000-10000 |
| Glutathione reduced (GSH) | 4300 | 1000-9000 |
| N-2-hydroxyethylpiperazine-N'-2-ethansulfonic acid (HEPES) | 4000 | 1000-10000 |
| Lactobionic Acid | 2100 | 1000-9000 |
| Histidine | 1550 | 50-4000 |
| D-Trehalose | 1000 | 50-4000 |
| D-Raffinose Pentahydrate | 1000 | 100-3000 |
| Calcium D-Gluconate | 1000 | 100-3000 |
| Sodium Chloride | 960 | 50-3000 |
| Sodium Citrate | 900 | 50-3000 |
| Potassium Chloride | 890 | 50-2000 |
| L-Alanine-L-Glutamine (not in ES2) | 880 | 50-3000 |
| Glutamic acid (not in ES2) | 700 | 50-3000 |
| Cysteine | 700 | 50-3000 |
| Arginine | 600 | 50-2000 |
| Ribose | 460 | 50-2000 |
| Tryptophan | 450 | 20-2000 |
| Sodium Pyruvate | 420 | 20-2000 |
| Carnitine | 400 | 20-2000 |
| Ascorbic Acid (vitamin C) | 380 | 20-1500 |
| $KH_2PO_4$ | 300 | 50-2000 |
| Glucose | 200 | 20-1500 |
| Ornithine | 200 | 20-1000 |
| Glycine | 40 | 5-500 |
| Glutathione disulfide (GSSG) | 20 | 5-500 |
| Adenine | 10 | 1-100 |
| Biotin (vitamin H) | 10 | 1-100 |

Example 2

The aim of this study was to assess cold storage of porcine kidneys using ES2, an organ preservation solution according to the current invention as described in Example 1, that does not include taurine, l-alanine-l-glutamine and glutamic acid. The results were compared with cold storage using Histidine-Tryptophan-Ketoglutarate, the clinical gold standard cold storage preservation solution. To this end, both preservation solutions were assessed using the isolated perfused porcine kidney model (IPPK) employing warm ischemically damaged (WI) kidneys.

TABLE 1

| Composition of HTK and ES2 | | |
|---|---|---|
| | HTK | ES2 |
| Electrolytes | low sodium, low potassium | high sodium, low potassium |
| Colloid | — | polyethylene glycol (PEG) |
| Impermeants | mannitol | raffinose, trehalose, lactobionic acid, Na, Ca, Mg-gluconate |
| Buffers | histidine | HEPES, $KH_2PO_4$, Sodium Citrate |
| Antioxidants | — | Reduced glutathione, glutathione disulfide |
| Metabolites | alpha-ketoglutarate | adenine, glucose, ribose, pyruvate |
| Amino acids | tryptophan | arginine, carnitine, cysteine, glycine, histidine, ornithine, tryptophan |
| Vitamins | — | Vitamin C, H |
| Viscosity at 21° C. (centiPoise) | 1.8 | 2.8 |
| Osmolarity (mmol/l) | 316 | 390 |
| Oncotic pressure (mmHg) | 4 | 25 |

Introduced by Hemingway in 1931, the isolated perfused porcine kidney model (IPPK) can provide useful information for preclinical testing of new preservation techniques studies since the porcine kidney is comparable to the human kidney with regards to physiology, immunity and size. Moreover, slaughterhouse kidneys or kidneys from animals used in other experiments can be employed, which is in accordance with the 3R principle (replacement, refinement, reduction) as postulated by Russell and Burch in 1959.

Materials and Methods

The experiments were performed in accordance with the German legislation governing animal studies following the 'Guide for the care and use of Laboratory Animals' (NIH publication, 8$^{th}$ edition, 2011) and the Directive 2010/63/EU on the protection of animals used for scientific purposes (Official Journal of the European Union, 2010). Official permission was granted from the governmental animal care and use office (LANUV Nordrhein-Westfalen, Recklinghausen, Germany).

Three groups (n=5 per group) were studied with kidneys retrieved without WI, washed out and cold stored for 24 h in HTK serving as Control group. In the ES2-WI and HTK-WI groups, kidneys were subjected to 45 min WI and consequently washed out and cold stored in their respective solutions.

Female Landrace pigs (45.7±1.1 kg) from a disease-free barrier breeding facility were housed in fully air conditioned rooms (22° C.) and allowed to acclimatize to their surroundings for a minimum of seven days and fasted for 12 h before surgery. The animals were premedicated with 8 mg/kg azaperone (Stresnil®, Janssen-Cilag GmbH, Neuss, Germany), 15 mg/kg ketamine (Ceva GmbH, Duesseldorf, Germany) and 10 mg atropine (1 ml/1% atropine sulfate, Dr. Franz Köhler Chemie GmbH, Bensheim, Germany) administrated intramuscularly. General anesthesia was induced by 2 mg/kg propofol (Fresenius Kabi Deutschland GmbH, Bad Homburg, Germany) administrated intravenously (IV), followed by intubation and mechanical ventilation with 1.5 Vol % isoflurane (Forene®, Abbot GmbH & Co. KG. Wiesbaden, Germany) and oxygen with continuous IV infusion of 0.02 mg/h/kg fentanyl (KG Rotexmedica GmbH, Trittau, Germany). After a midline laparotomy, both kidneys were explanted with or without induction of WI. Directly after retrieval, 1 L of whole blood was collected into CPD bags (Fenwal Inc., Illinois, USA) and stored at 4° C. for ex-vivo reperfusion. The animals were euthanized by IV administration of 1 ml/kg BW pentobarbital (Narcoren®, MERIAL GmbH, Hallbergmoss, Germany).

Kidney Explantation and Wash Out

For induction of WI, both the renal artery and vein were clamped for 45 min followed by retrieval and washout directly or after 45 min WI via the renal artery. For wash out, either 500 ml of cold HTK or ES2 solution was used at a hydrostatic pressure of 100 cm $H_2O$. During wash out, the renal vein as well as the ureter were canulated for sample collection during reperfusion. Thereafter the kidneys were weighed and stored in the respective preservation solutions at 4° C. After 24 h CS, kidney function and damage parameters were assessed using the IPPK model.

Reperfusion

As reperfusion medium, modified Krebs-Henseleit-Buffer (9.6 g/L, Sigma-Aldrich Chemie GmbH, Steinheim, Germany), calcium chloride (0.37 g/L, Sigma-Aldrich Chemie GmbH), 8.4% sodium hydrogen carbonate (25 ml/L, Fresenius GmbH, Germany), creatinine (1 mmol/L, Sigma-Aldrich Chemie GmbH), heparin (3000 IU/L, Ratiopharm GmbH, Ulm, Germany) and Fibrisol (3 g/L, Muscalla, Vierheim, Germany) were dissolved in 800 ml water for injection (Ampuwa, Fresenius Kabi AG, Bad Homburg, Germany) and 200 ml of autologous non leucocyte depleted whole blood was added to the mixture.

After CS, kidneys were weighed and placed into an organ reservoir, filled with 1 L reperfusion medium pre-warmed to 38° C. using a heating bath (HAAKE DC30, W13, Thermo Electron GmbH, Karlsruhe, Germany) and pressure controlled reperfused for 60 min at a pre-set mean arterial pressure of 85 mmHg. The reperfusion medium was circulated by a computer controlled pulsatile roller pump (IS-MATEC®, MPC Standard, Gladburg, Switzerland) through an oxygenator (Hilite® 2400 LT, MEDOS, Stolberg, Germany) and bubble trap to the renal artery and exited the kidney freely into the organ reservoir. A pressure (MLT844, AD Instruments GmbH, Spechbach, Germany) and flow sensor (ME2PXL1072 sensor, TS410 flow meter module, Transonic Systems Inc., Ithaca, N.Y., USA) were connected to the renal artery, and the data was collected using a data acquisition system (PowerLab 8/30, AD Instruments GmbH, Spechbach, Germany). Renal blood flow (RBF), mean arterial pressure (MAP) and temperature were continuously recorded and stored using Lab Chart 7 software (AD Instruments GmbH). The intrarenal vascular resistance (IRR) was calculated as MAP/RBF/100 g.

The reperfusion medium was continuously oxygenated with carbogen (95% oxygen/5% carbon dioxide), achieving an arterial partial oxygen pressure ($pO_2$) of over 500 mmHg throughout the whole reperfusion time. Arterial and venous $pO_2$ and pH levels were measured using a blood gas analyzer (ABL 725, Radiometer GmbH, Willich, Germany). Urine was collected separately and the perfusate volume was replenished every 15 min to compensate for the excreted urine volume. Urine output was recorded and samples were collected at 5, 15, 30, 45 and 60 min during reperfusion for determination of sodium, creatinine and urine protein concentrations. Venous perfusate samples were taken at 5, 15, 30, 45 and 60 min and analyzed for sodium and creatinine levels. Using venous perfusate and urine levels, creatinine clearance (CrCl, urine creatinine×urinary flow/plasma creatinine) and fractional excretion of sodium (FENa, urinary sodium×plasma creatinine)/(plasma sodium×urinary creatinine)×100%) were calculated. Renal metabolic activity was approximated by calculation of oxygen consumption using arterial and venous $pO_2$ values (($p_aO_2-p_vO_2$)×flow rate/kidney weight).

Neutrophil Gelatinase-Associated Lipocalin

Urinary levels of the acute tubular injury marker neutrophil gelatinase-associated lipocalin (NGAL, Kit 044, BioPorto Diagnostics, Gentofte, Denmark) were determined using enzyme linked immunosorbent assay (ELISA) according to the manufacturer's instructions. The absorbance was detected at 450 nm using a microplate reader (Infinite M200, Tecan Austria GmbH, Grödig, Austria).

Oxidative Status

For the assessment of the oxidative status of kidney tissue, reduced (GSH) and oxidized glutathione (GSSG) levels were determined. Also, thiobarbituric acid reactive substances (TBARS) as a byproduct of lipid peroxidation were determined. Frozen tissue was homogenized in ice-cold phosphate buffered saline tissue (10% w/v), then centrifuged for 5 min at 4000 g and supernatants were stored at −20° C. TBARS, GSH and GSSG concentrations were expressed in μmol per gram protein. The renal tissue protein content was assessed using bicinchoninic acid assay (BCA, Fermentas, Lithuania). All measurements were performed using a Saphire II spectrofluorometer (Tecan Austria GmbH). The ratio of reduced to oxidized glutathione was thereafter calculated.

Histology

After reperfusion, kidney tissue slices were fixed in 10% formalin, and stored in 4% formalin before paraffin embedding. The specimen were stained by Periodic acid-Schiff (PAS) reaction and examined, blinded to the experimental conditions. Twenty Bowman's capsule and glomerular cross-section areas as well as tubular outer diameter were measured per slide under 20× magnification using Nanozoomer digital pathology system software (Hamamatsu Photonics Deutschland GmbH, Herrsching am Ammersee, Germany).

Statistical Analysis

Statistical analysis was performed by ANOVA followed by Bonferroni post-test correction using the GraphPad Prism 5.01 software package (GraphPad Software Inc, San Diego, Calif., USA). Data are presented as mean±SEM. Area under the curve (AUC) was calculated individually and compared using Kruskal-Wallis with Dunn's post-test. A p value<0.05 was considered statistically significant.

Results

Kidney weights after organ retrieval did not differ significantly (Control vs. HTK-WI vs. ES2-WI; 115±8 vs. 119±12 vs. 116±9 g resp.), however kidneys in both the HTK washed out control group and the HTK-WI group gained weight after washout which differed from the ES2-WI group. The time needed for washout of 500 ml preservation solution did not differ (Control vs. HTK-WI vs. ES2-WI; 13±1 vs. 26±6 vs. 18±3 min resp.).

Reperfusion Parameters

During reperfusion, the intrarenal resistance was significantly lower in both Control and ES2-WI groups compared to the HTK-WI group.

Renal Function

In the Control group, the CrCl rate was higher compared to the ES2-WI and HTK-WI groups. As a marker for acute renal failure, FENa was better in the Control group in comparison to the ES2-WI and HTK-WI groups.

Oxygen consumption was higher in the Control group and in the ES2-WI groups at all time points compared to HTK-WI whereas controls did not differ from ES2-WI.

Both Control and ES2-WI groups maintained a physiological metabolic acid-base balance during reperfusion in contrast to HTK-WI, which demonstrated significantly lower venous pH levels compared to ES2-WI at all time points.

At 5 min reperfusion, both WI groups demonstrated higher urinary protein concentrations compared to Control. Thereafter, CS-HTK urinary protein concentrations were higher than Control and ES2-WI, with ES2-WI not differing from controls.

The total output of urine was higher in controls compared to both WI groups, however less output of urine was observed in kidneys in the HTK-WI group compared to ES2-WI.

Acute tubular injury was more severe in the HTK-WI group compared to controls as expressed by significantly higher urinary NGAL levels. Increased lipid peroxidation as reflected by post-reperfusion tissue TBARS levels were observed in the HTK-WI group compared to the Control group. Moreover, a lower ratio of reduced to oxidized glutathione was seen in both Control and HTK-WI groups compared to ES2-WI.

Histology

Microthrombi were present in the glomeruli in the HTK-WI group only. Also, the Bowman's capsule cross-section area was significantly enlarged in HTK-WI compared to Control and ES2-WI. The same trend was observed with tubular diameter. Intratubular protein was present only in the HTK-WI group due to increased permeability of the glomerular capillary walls.

Conclusion

ES2 preservation solution was compared to HTK for 24 h CS preservation of 45 min WI damaged kidney grafts, employing non-WI damaged kidneys, cold stored for 24 h in HTK as controls. Kidney function was significantly lower in ES2-WI and HTK-WI compared to controls as expressed by lower creatinine clearance rates. Also, renal tubular function was significantly lower in ES2-WI and HTK-WI compared to controls as reflected by fractional excretion of sodium. ES2 preserved WI-damaged grafts demonstrated significantly lower IRR, urinary protein concentrations and levels of oxidative stress markers, as well as higher oxygen consumption compared to HTK-WI. Also, a higher urine output and better maintenance of acid-base balance was observed in ES2-WI when compared to HTK-WI. In conclusion, this study demonstrated advantages of ES2 solution in comparison to the HTK solution for preservation of WI-damaged, cold stored kidney grafts.

Example 3

The aim of this study was the assessment of the Example Solution (ES), an organ preservation solution according to the current invention and as described in Example 1, for venous systemic oxygenated persufflation (VSOP) and oxygenated mechanical perfusion (MP) preservation of kidneys for transplantation. The results were compared with cold storage (CS) using ES and Histidine-Tryptophan-Ketoglutarate preservation solution (HTK), the clinical gold standard organ preservation solution worldwide. To this end, the isolated perfused porcine kidney model (IPPK) was used employing warm ischemically damaged (WI) kidneys.

TABLE 1

| Composition of HTK and ES | | |
|---|---|---|
| | HTK | ES |
| Electrolytes | low sodium, low potassium | high sodium, low potassium |
| Colloid | — | polyethylene glycol (PEG) |
| Impermeants | mannitol | raffinose, trehalose, lactobionic acid, Na, Ca, Mg-gluconate |
| Buffers | histidine | HEPES, $KH_2PO_4$, Sodium citrate |
| Antioxidants | — | taurine, glutathione reduced, glutathione disulfide |
| Metabolites | alpha-ketoglutarate | adenine, glucose, ribose, pyruvate |
| Amino acids | tryptophan | L-alanine-L-glutamine, glutamic acid, arginine, carnitine, cysteine, glycine, histidine, ornithine, tryptophan |
| Vitamins | — | Vitamin C (ascorbic acid), Vitamin H (biotin) |
| Viscosity at 21° C. (centiPoise) | 1.8 | 2.9 |
| Osmolarity (mmol/l) | 316 | 395 |
| Oncotic pressure (mmHg) | 4 | 25 |

Introduced by Hemingway in 1931, the isolated perfused porcine kidney model (IPPK) can provide useful information for preclinical testing of new preservation techniques studies since the porcine kidney is comparable to the human kidney with regards to physiology, immunity and size. Moreover, slaughterhouse kidneys or kidneys from animals used in other experiments can be employed, which is in accordance with the 3R principle (replacement, refinement, reduction) as postulated by Russell and Burch in 1959. In this study the efficacy of ES preservation solution in combination with aerobiosis by VSOP or oxygenated MP was compared to CS using ES or HTK for 24-hour preservation of extensively warm ischemia (WI) damaged kidneys using the isolated perfused porcine kidney model (IPPK). To this end, ES preservation solution was employed which constitutes taurine, L-alanine-L-glutamine and glutamic acid as well as a colloid, impermeants and potent buffers, allowing application in VSOP, MP as well as CS preservation.

Material and Methods

Experimental Protocols

The experiments were performed in accordance with the German legislation governing animal studies following the 'Guide for the care and use of Laboratory Animals' (NIH publication, 8$^{th}$ edition, 2011) and the Directive 2010/63/EU on the protection of animals used for scientific purposes (Official Journal of the European Union, 2010). Official permission was granted from the governmental animal care and use office (LANUV Nordrhein-Westfalen, Recklinghausen, Germany).

Female German Landrace pigs (48±2 kg) from a disease-free barrier breeding facility were housed in fully air conditioned rooms (22° C. room temperature, 50% relative humidity) and allowed to acclimatize to their surroundings for a minimum of seven days and fasted for 12 h before surgery with free access to water. The animals were premedicated with 8 mg/kg body weight (BW) azaperone (Stresnil®, Janssen-Cilag GmbH, Neuss, Germany), 15 mg/kg BW ketamine (Ceva GmbH, Duesseldorf, Germany) and 10 mg atropine (1 ml/1% atropine sulfate, Dr. Franz Köhler Chemie GmbH, Bensheim, Germany) administered intramuscularly. General anesthesia was induced by 2 mg/kg BW propofol (Fresenius Kabi Deutschland GmbH, Bad Homburg, Germany) administered intravenously, followed by intubation and mechanical ventilation with 1.5 Vol % isoflurane (Forene®, Abbot GmbH & Co. KG. Wiesbaden, Germany) and oxygen with continuous intravenous infusion of 0.02 mg/h/kg BW fentanyl (KG Rotexmedica GmbH, Trittau, Germany).

In the CS-HTK, CS-ES, MP-ES and VSOP-ES groups, kidneys were subjected to 45 min warm ischemia and subsequently washed out and preserved for 24 h using their respective methods (n=5 per group). Kidneys recovered without warm ischemia, washed out and cold stored for 24 h in HTK served as negative control group (n=5). After the preservation period, kidney function and damage parameters were assessed using the IPPK model. Directly after recovery, 1 L of whole blood was collected into citrate-phosphate-dextrose bags (Fenwal Inc., Illinois, USA) and stored at 4° C. for ex-vivo reperfusion. The animals were euthanized by IV administration of 1 ml/kg BW pentobarbital (Narcoren®, Merial GmbH, Hallbergmoss, Germany).

Kidney Retrieval

After a midline laparotomy, both kidneys were explanted directly or with exposure to warm ischemia by clamping both the renal artery and vein for 45 min followed by recovery and washout via the renal artery. For washout, either 500 ml of cold ES or HTK solution was used at a hydrostatic pressure of 100 cm $H_2O$. During washout, the renal vein and ureter were canulated for sample collection during reperfusion. Thereafter, kidneys were weighed and for the CS-HTK, CS-ES and control groups, stored for 24 h on melting ice in their respective preservation solutions.

VSOP

In the VSOP-ES group, kidneys stored at 4° C. in ES were persufflated through the renal vein for 24 h. Pure medical grade oxygen was moisturized using a wash bottle and introduced into the kidney at a constant pressure of 18 mmHg and a flow of 1 L/min.

MP

Directly after washout, kidneys in the MP-ES group were oxygenated perfused in a pulsatile manner at 25 mmHg mean arterial pressure using a computer controlled pulsatile roller pump (ISMATEC®, MPC Standard, Gladburg, Switzerland) through an oxygenator (Hilite© 2400 LT, MEDOS, Stolberg, Germany) and a bubble trap to the renal artery and exited the kidney freely into the organ reservoir. A pressure (MLT844, AD Instruments GmbH, Spechbach, Germany) and flow sensor (ME2PXL1072, TS410 flow meter module, Transonic Systems Inc., Ithaca, N.Y., USA) were connected to the renal artery and the data was collected using a data acquisition system (PowerLab 8/30, AD Instruments GmbH, Spechbach, Germany). The perfusate temperature was kept at 4° C. using a cooling system (refrigerated immersion cooler C1G, Grant Instruments, Shepreth, England), thermo bath (HAAKE W13, Thermo Electron GmbH, Karlsruhe, Germany) with a thermo regulator (HAAKE DC30) and a heat exchanger integrated into the oxygenator. The perfusate was continuously oxygenated with medical grade oxygen, achieving an arterial partial oxygen pressure ($pO_2$) of over 700 mmHg throughout the MP period. Arterial $pO_2$ levels were measured using a blood gas analyzer (ABL 725, Radiometer GmbH, Willich, Germany). Perfusate flow, mean arterial pressure and temperature were continuously recorded and stored using Lab Chart 7 software (AD Instruments GmbH).

Reperfusion

As reperfusion medium, a modified Krebs-Henseleit-Buffer and autologous non-leucocyte depleted whole blood mixture was used. After the preservation period, kidneys were weighed and placed into an organ reservoir, filled with 1 L reperfusion medium pre-warmed to 38° C. and pressure controlled perfused for 60 min at a pre-set mean arterial pressure of 85 mmHg using the same perfusion setup as applied for MP.

The reperfusion medium was continuously oxygenated with carbogen (95% oxygen/5% carbon dioxide), achieving an arterial partial oxygen pressure ($pO_2$) of over 500 mmHg throughout the reperfusion period. Arterial and venous $pO_2$ and pH levels were measured at 5, 15, 30, 45 and 60 min using a blood gas analyzer (ABL 725, Radiometer GmbH). Renal metabolic activity was approximated by calculation of oxygen consumption using arterial and venous $pO_2$ values (($p_aO_2-pO_2$)×flow/kidney weight). The intrarenal resistance was calculated as mean arterial pressure/renal flow/100 g. Urine samples were collected at 5, 15, 30, 45 and 60 min during reperfusion for determination of sodium, creatinine and urine protein concentrations and the total urine output was recorded. The perfusate volume was replenished every 15 min to compensate for the excreted urine volume. Venous perfusate samples were taken at 5, 15, 30, 45 and 60 min and analyzed for sodium and creatinine levels. Using venous perfusate and urine levels, creatinine clearance (urine creatinine×urinary flow/plasma creatinine) and fractional excretion of sodium ((urinary sodium×plasma creatinine)/(plasma sodium×urinary creatinine))×100%) were calculated.

Neutrophil Gelatinase-Associated Lipocalin

Urinary levels of the acute tubular injury marker neutrophil gelatinase-associated lipocalin (NGAL, Kit 044, BioPorto Diagnostics, Gentofte, Denmark) were determined at the end of reperfusion using enzyme linked immunosorbent assay (ELISA) according to the manufacturer's instructions. The absorbance was detected at 450 nm using a microplate reader (Infinite M200, Tecan Austria GmbH, Grödig, Austria).

Oxidative Status

For assessment of the oxidative status, frozen tissue samples taken after reperfusion were homogenized in ice-cold phosphate buffered saline (10% w/v), then centrifuged for 5 min at 4000 g and the supernatants were stored at −20° C. Concentrations of reduced (GSH) and oxidized glutathione (GSSG) were determined as described previously. The ratio of GSH to GSSG was then calculated. Also, tissue samples were analyzed for thiobarbituric acid reactive substances (TBARS) as a byproduct of lipid peroxidation and expressed in μmol per gram protein. The renal tissue protein content was assessed using bicinchoninic acid assay (BCA, Fermentas, Vilnius, Lithuania). All measurements were performed using a Saphire II spectrofluorometer (Tecan Austria GmbH, Grödig, Austria).

Histology

After reperfusion, kidney tissue slices were fixed in 10% formalin for 24 h and embedded in paraffin. Four-micron sections were stained either with the periodic acid-Schiff reagent and counterstained with hematoxylin (PAS) and digitized using a whole-slide scanner (Hamamatsu NanoZoomer 2.0HT). Twenty Bowman's capsule' areas were measured per slide under 20× magnification using Hamamatsu digital pathology system software (Hamamatsu Photonics Deutschland GmbH, Herrsching am Ammersee, Germany). All analyses where performed in a blinded fashion.

Statistical Analysis

Values are presented as mean±SEM. After proving the assumption of normality, statistical analysis was performed by one-way analysis of variance (ANOVA) followed by Tukey multiple comparison test, using the GraphPad Prism 6.01 software package (GraphPad Software Inc, San Diego, Calif., USA). The area under the curve (AUC) was calculated individually for continuous parameters and mean AUC were compared using Kruskal-Wallis with Dunn's post-test. A p value<0.05 was considered statistically significant.

Results

After explantation, kidney weights did not differ significantly (126±11 vs. 120±8 vs. 121±11 vs. 124±7 vs. 108±2 g; CS-HTK vs. CS-ES vs MP-ES vs VSOP-ES vs. control respectively). During washout, kidneys in the CS-ES, MP-ES and VSOP-ES groups lost weight in contrast to kidneys in both the CS-HTK and control groups which gained weight, suggestive of intrarenal edema formation by extravasation of the HTK solution (−17±2 vs.−17±4 vs.−11±2 vs. 22±2 vs. 27±4 g resp., p<0.0001). The time needed for washout of 500 ml preservation solution did not differ significantly (CS-HTK vs. CS-ES vs MP-ES vs VSOP-ES vs. control; 26±6 vs. 18±3 vs. 18±4 vs. 17±4 vs. 15±2 min resp.).

Renal Function

The AUC for creatinine clearance was lower in the CS-HTK group compared to controls. As a marker for acute tubular injury, fractional excretion of sodium was higher in CS-HTK compared to VSOP-ES and controls. Also, for both creatinine clearance and fractional excretion of sodium, CS-ES, MP-ES and VSOP-ES did not differ significantly from the non-warm ischemic control group. Kidneys preserved by CS-ES and VSOP-ES maintained a physiological metabolic acid-base homeostasis during reperfusion in contrast to CS-HTK, which demonstrated significantly lower venous pH levels during the entire reperfusion period.

The total output of urine of kidneys in the CS-HTK group was lower compared to the CS-ES, MP-ES, VSOP-ES and control groups (Table 1). The CS-HTK group demonstrated higher urinary protein concentrations compared to VSOP-ES and controls. From 15 min of reperfusion, urinary protein concentrations were more than 3-fold higher in CS-HTK than in CS-ES, MP-ES, VSOP-ES and controls. Acute tubular injury was more severe in the CS-HTK group compared to controls as expressed by higher urinary NGAL levels (Table 1). Intrarenal resistance was higher in CS-HTK compared to CS-ES and controls. Although not statistically significant, the intrarenal resistance was approximately 5-fold lower in the VSOP-ES group compared to CS-HTK (p=0.0524) and a trend was seen in increasing intrarenal resistance in the MP-ES group. Metabolic activity as expressed by oxygen consumption was lower in CS-HTK compared to CS-ES and controls throughout the reperfusion period. The VSOP-ES group demonstrated a 3-fold higher oxygen consumption compared to CS-HTK and did not differ from controls.

Oxidative Status

Reduced lipid peroxidation, as reflected by post-reperfusion tissue TBARS concentrations, was observed in VSOP-ES compared to MP-ES, with VSOP-ES and CS-ES having concentrations similar to controls (Table 1). A lower GSH/GSSG ratio was seen in both the CS-HTK and control groups compared to CS-ES, MP-ES and VSOP-ES with a lower ratio in MP-ES than in VSOP-ES (Table 1).

TABLE 1

Post-reperfusion parameters

| | CS-HTK | CS-ES | MP-ES | VSOP-ES | control |
|---|---|---|---|---|---|
| Total urine (ml) | 86 ± 41[a] | 196 ± 28 | 332 ± 54 | 304 ± 43 | 443 ± 58 |
| NGAL (ng/ml) | 74.8 ± 9.0[b] | 52.7 ± 3.7 | 57.4 ± 12.9 | 50.1 ± 5.0 | 29.2 ± 6.1 |
| TBARS (μmol/g) | 0.63 ± 0.05 | 0.48 ± 0.06 | 0.67 ± 0.09[c] | 0.42 ± 0.01 | 0.45 ± 0.03 |
| GSH/GSSG ratio | 1.6 ± 0.1[d] | 4.9 ± 0.5 | 3.6 ± 0.4[e] | 5.6 ± 0.5 | 1.7 ± 0.1[f] |

[a]CS-HTK vs. CS-ES p < 0.05; CS-HTK vs. MP-ES p < 0.001, CS-HTK vs. VSOP-ES p < 0.01, CS-HTK vs. control p < 0.0001;
[b]CS-HTK vs. control p < 0.01;
[c]MP-ES vs. VSOP-ES p < 0.05;
[d]CS-HTK vs. CS-ES and VSOP-ES p < 0.0001, CS-HTK vs. MP-ES p < 0.01,
[e]MP-ES vs. VSOP-ES p < 0.01;
[f]CS-ES and VSOP-ES vs.control p < 0.0001, MP-ES vs. control p < 0.01.

Histology

Kidney cross sections after 1 h reperfusion showed both macroscopically and microscopically blood remnants in the medullary and cortical regions in the CS-HTK preserved kidneys only. Also in the CS-HTK group, the Bowman' space was significantly enlarged compared to CS-ES, MP-ES, VSOP-ES and control groups. Moreover, intratubular protein was observed in the HTK group, which is in accordance with the high urine protein concentrations during reperfusion.

Conclusions

VSOP, MP and CS using ES preservation solution were compared to HTK for 24-hour preservation of 45 minutes warm ischemia (WI) damaged kidney grafts, employing non-WI damaged kidneys, cold stored for 24 hour in HTK as controls. Renal function and renal tubular injury did not differ significantly in the VSOP-ES, MP-ES and CS-ES groups from the non-warm ischemically damaged controls. Urine production was significantly higher in the VSOP-ES, MP-ES and CS-ES groups compared to CS-HTK. Reduced lipid peroxidation was observed in VSOP-ES and CS-ES compared to CS-HTK, with concentrations similar to controls. This study demonstrated the superiority of ES preservation solution for VSOP, oxygenated MP and CS in comparison to the gold standard HTK solution and improvement of oxidative status as well as metabolic and functional recovery of WI-damaged kidney grafts. ES preservation solution in combination with VSOP resulted in improved preservation quality of WI-damaged porcine kidney grafts which was comparable to non-WI damaged kidneys using HTK. Therefore, ES applied for oxygenated preservation has the potential to resuscitate extensively warm ischemia-damaged kidneys.

The invention claimed is:

1. An aqueous organ preservation solution comprising taurine, and L-alanine-L-glutamine, glutamic acid, and a colloid;
   wherein the taurine is at a concentration in the range of 100 to 10,000 mg/L;
   wherein the L-alanine-L-glutamine is at a concentration in the range of 50 to 3,000 mg/L;
   wherein the glutamic acid is at a concentration in the range of 50 to 3000 mg/L;
   wherein the colloid is polyethylene glycol with a molecular weight in the range of 10,000 to 55,000 Dalton; and
   wherein the polyethylene glycol is at a concentration in the range of 10,000 to 30,000 mg/L.

2. The aqueous organ preservation solution according to claim 1 further comprising: an anti-oxidant, an electrolyte, an impermeant, an amino acid, a vitamin and at least 2 buffer compounds.

3. The aqueous organ preservation solution according to claim 1 further comprising at least 2 impermeants, and at least 2 anti-oxidants.

4. The aqueous organ preservation solution according to claim 1, further comprising glutathione and/or glutathione disulfide.

5. The aqueous organ preservation solution according to claim 4, comprising glutathione and glutathione disulphide, wherein the ratio between glutathione and glutathione disulfide is in the range between 1:10 and 10:1.

6. The aqueous organ preservation solution according to claim 1, further comprising glutathione disulfide at a concentration in the range of 5 to 500 mg/L.

7. The aqueous organ preservation solution according to claim 1, wherein the aqueous solution further comprises at least one vitamin selected from vitamin B1, vitamin B3, vitamin B6, vitamin B12, vitamin C and/or vitamin E.

8. The aqueous organ preservation solution according to claim 1, further comprising at least one buffer compound, wherein the at least one buffer compound is selected from N-2-hydroxyethylpiperazine-N'-2-ethanesulfonic acid, $NaHCO_3$, $KH_2PO_4$, sodium phosphate, sodium citrate and/or histidine.

9. The aqueous organ preservation solution according to claim 1, further comprising at least one electrolyte, wherein the at least one electrolyte is selected from sodium, wherein the concentration is from 50 to 200 mmol/L;
   potassium, wherein the concentration is from greater than 0 to 25 mmol/L;
   calcium, wherein the concentration is from greater than 0 to 10 mmol/L;
   magnesium, wherein the concentration is from greater than 0 to 20 mmol/L;
   chloride ions, wherein the concentration is from greater than 0 to 50 mmol/L.

10. The aqueous organ preservation solution according to claim 1, further comprising at least two impermeants, wherein the at least two impermeants are selected from calcium gluconate, sodium gluconate, magnesium gluconate, potassium gluconate, lactobionic acid, trehalose, ribose and/or raffinose.

11. The aqueous organ preservation solution according to claim 1, wherein the aqueous solution further comprises one or more amino acids and/or peptides.

12. The aqueous organ preservation solution according to claim 1, wherein the aqueous solution further comprises cysteine, glutamate, carnitine, ornithine, arginine, histidine, tryptophan and/or glycine.

13. The aqueous organ preservation solution according to claim 1, wherein the aqueous solution further comprises glucose, ribose, pyruvate and/or a fatty acid.

14. The aqueous organ preservation solution according to claim 1, wherein the aqueous solution has an oncotic pressure in the range of 10 to 40 mmHg.

15. The aqueous organ preservation solution according to claim 1, wherein the aqueous solution has a pH in the range of 7.2 to 7.6.

16. The aqueous organ preservation solution according to claim 1, wherein the aqueous solution has an osmolarity in the range of 300 to 420 mosm.

17. The aqueous organ preservation solution according to claim 1, wherein the temperature of the aqueous solution is in the range of 0° C. to 20° C. or 20° C. to 40° C.

18. An organ preservation composition for the preparation of an aqueous organ preservation solution of claim 1, wherein the organ preservation composition is a solid that is configured to result in the aqueous organ preservation solution when mixed with an amount of water.

19. A method of preservation, comprising:
   utilizing the aqueous organ preservation solution according to claim 1 for the preservation of an organ or parts of an organ, wherein said use comprises oxygenated perfusion of said organ or part thereof with said aqueous organ preservation solution.

20. The method according to claim 19, wherein said perfusion comprises gravitational and/or mechanical perfusion.

21. The method according to claim 19, wherein the organ or part of an organ is of human origin.

22. The method according to claim 21, wherein the organ or part of an organ is a kidney, liver, lung, heart, pancreas and/or intestine.

23. A method for preparing the aqueous organ preservation solution according to claim 1 comprising the steps of:
   a) providing an organ preservation composition of taurine, L-alanine-L-glutamine, glutamic acid and polyethylene glycol;
   b) providing water; and
   c) mixing the organ preservation composition with the water, thereby obtaining the aqueous organ preservation solution of claim 1.

* * * * *